United States Patent
Nordstrom et al.

(10) Patent No.: US 10,204,212 B1
(45) Date of Patent: Feb. 12, 2019

(54) FACILITATING MEDICATION ADMINISTRATION

(71) Applicant: Allscripts Software, LLC, Chicago, IL (US)

(72) Inventors: Wyatt Nordstrom, Raleigh, NC (US); Mark Christopher Kenney, Downington, PA (US); Martine Shendge, Lancaster, PA (US); Ariel Noel Norton, Raleigh, NC (US); Paul Robert Fritz, Raleigh, NC (US); Ramakant Bhandaru, Chester Springs, PA (US); Peter John Barber, Raleigh, NC (US); James Palmer, Phoenixville, PA (US); Elizabeth Sullivan, Wake Forest, NC (US); Carin Mann, Raleigh, NC (US); Mohammed Wahab, Carol Stream, IL (US)

(73) Assignee: Allscripts Software, LLC, Chicago, IL (US)

( * ) Notice: Subject to any disclaimer, the term of this patent is extended or adjusted under 35 U.S.C. 154(b) by 794 days.

(21) Appl. No.: 14/587,767

(22) Filed: Dec. 31, 2014

Related U.S. Application Data

(60) Provisional application No. 62/036,566, filed on Aug. 12, 2014.

(51) Int. Cl.
*G06F 19/00* (2018.01)
*G16H 10/60* (2018.01)

(52) U.S. Cl.
CPC ........ *G06F 19/3456* (2013.01); *G06F 19/322* (2013.01); *G16H 10/60* (2018.01)

(58) Field of Classification Search
None
See application file for complete search history.

(56) References Cited

U.S. PATENT DOCUMENTS

| | | | |
|---|---|---|---|
| 4,857,713 A * | 8/1989 | Brown | A61B 5/117 705/3 |
| 7,155,306 B2 | 12/2006 | Haitin | |
| 2005/0004700 A1 | 1/2005 | DiMaggio | |
| 2006/0136167 A1* | 6/2006 | Nye | A61B 5/02055 702/127 |
| 2007/0005396 A1* | 1/2007 | Lee | G06F 19/3456 705/3 |
| 2007/0233521 A1 | 10/2007 | Wehba | |
| 2011/0010195 A1 | 1/2011 | Cohn | |
| 2011/0246224 A1 | 10/2011 | Green et al. | |
| 2012/0323602 A1 | 12/2012 | Ryan | |

OTHER PUBLICATIONS

Information Disclosure Statement (IDS) Letter Regarding Common Patent Applications(s), dated Feb. 6, 2018.
Yongxing Deng, Vincent Siao, Josh Smith & Stephanie Hornung; Asana Blog, Aug. 27, 2013, retrieved Sep. 7, 2017 from https://blog.asana.com/2013/08/mergetaske/ (Year: 2013).

\* cited by examiner

*Primary Examiner* — Michael Tomaszewski
(74) *Attorney, Agent, or Firm* — Peter Zura; Loza & Loza, LLP

(57) ABSTRACT

A medical software application including an interface which is configured to allow for automatic barcode scanning of barcodes associated with patients and medications for medication administration is further configured to display confirmation of each of the "five rights" of medication administration.

20 Claims, 9 Drawing Sheets

FACILITATING MEDICATION ADMINISTRATION

CROSS-REFERENCE TO RELATED APPLICATION

The present application is a U.S. nonprovisional patent application of, and claims priority under 35 U.S.C. § 119(e) to, U.S. provisional patent application Ser. No. 62/036,566, filed Aug. 12, 2014, which provisional patent application is incorporated by reference herein.

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

COMPUTER PROGRAM LISTING

Submitted concurrently herewith via the USPTO's electronic filing system, and incorporated herein by reference, are computer program files including instructions, routines, and/or other contents of several computer programs. A table setting forth the name and size of files included in the computer program listing is included below.

| File Name | Creation Date | File Size (bytes) |
| --- | --- | --- |
| ASCIFY.txt | Aug. 12, 2014 16:40 | 37473 |
| mob1.txt | Aug. 12, 2014 16:41 | 22478505 |
| mob10.txt | Aug. 12, 2014 16:41 | 22475418 |
| mob11.txt | Aug. 12, 2014 16:41 | 22475075 |
| mob12.txt | Aug. 12, 2014 16:41 | 22474732 |
| mob13.txt | Aug. 12, 2014 16:41 | 22474389 |
| mob14.txt | Aug. 12, 2014 16:41 | 22474046 |
| mob15.txt | Aug. 12, 2014 16:41 | 22473703 |
| mob16.txt | Aug. 12, 2014 16:41 | 22473360 |
| mob17.txt | Aug. 12, 2014 16:41 | 22473017 |
| mob18.txt | Aug. 12, 2014 16:41 | 22472674 |
| mob19.txt | Aug. 12, 2014 16:41 | 22472331 |
| mob2.txt | Aug. 12, 2014 16:41 | 22478162 |
| mob20.txt | Aug. 12, 2014 16:41 | 22471988 |
| mob21.txt | Aug. 12, 2014 16:41 | 22471645 |
| mob22.txt | Aug. 12, 2014 16:41 | 22471302 |
| mob23.txt | Aug. 12, 2014 16:41 | 22470959 |
| mob24.txt | Aug. 12, 2014 16:41 | 22470616 |
| mob25.txt | Aug. 12, 2014 16:41 | 22470273 |
| mob26.txt | Aug. 12, 2014 16:41 | 22469930 |
| mob27.txt | Aug. 12, 2014 16:41 | 22469587 |
| mob28.txt | Aug. 12, 2014 16:41 | 12976474 |
| mob3.txt | Aug. 12, 2014 16:41 | 22477819 |
| mob4.txt | Aug. 12, 2014 16:41 | 22477476 |
| mob5.txt | Aug. 12, 2014 16:41 | 22477133 |
| mob6.txt | Aug. 12, 2014 16:41 | 22476790 |
| mob7.txt | Aug. 12, 2014 16:41 | 22476447 |
| mob8.txt | Aug. 12, 2014 16:41 | 22476104 |
| mob9.txt | Aug. 12, 2014 16:41 | 22475761 |
| readme.txt | Aug. 12, 2014 16:40 | 2830 |

One of these files, "readme.txt", contains instructions for extracting information from other of the files. These other files represent a compressed binary file that has been converted to ASCII format and split into multiple ascii files. These files can be converted back to a compressed .zip archive utilizing an assembly conversion program source code for which is contained in "ascify.txt". The readme file includes instructions for compiling and running this conversion program, and instructions for converting the other text files to a compressed, binary file.

The compressed, binary file includes source code written in C Sharp that can be compiled utilizing Microsoft Visual Studio. The target environment for implementations utilizing such source code is 32-bit or 64-bit Windows XP, Vista, or 7.

BACKGROUND OF THE INVENTION

The present invention generally relates to the use of a mobile device for healthcare provision and medical software therefore.

In healthcare practices, it is common for nurses administering medications to confirm the "five rights" of medication administration: right patient, right drug, right dose, right route, and right time.

Historically, nurses would manually confirm each of these rights prior to medication administration. As technology has developed, medication administration has evolved, and technology, such as bar code scanning, is utilized in many medication administration processes. For example, in an exemplary conventional bar code medication administration (BCMA) process, a nurse scans a barcode associated with a medication, and then scans a barcode printed on a patient's wristband, and software confirms the medication is the right medication for the right patient. Existing software may confirm other of the "five rights", but this confirmation is not exposed to a user, so a healthcare practitioner has to either trust that the software is confirming the "five rights", or manually confirm the "five rights".

Sometimes, however, a particular barcode is unreadable or cannot be scanned, or a barcode is not available. Frequently, medical software configured for barcode scanning will allow a user to bypass a scan feature when needed. Generally, however, this bypass feature requires a user to leave a scanning interface to enter required information for the bypass.

Further, it is common for nurses administering medications to review patient vitals and lab results. This information is commonly available in electronic health record software, but accessing it typically requires multi-step navigation through the software.

It is similarly important that nurses administering medications have access to allergy information.

In many cases, a clinician initially only cares about whether there are allergies or not and how severe they are. A low severity allergy is not as important as a high severity one. For patients with a long list of allergies, it is often hard to scan them to determine how severe they are and what a clinician needs to pay attention to. In some existing medical software, allergy information is truncated and a clinician needs to hover to find important information, which may be at the end of the list. Further, in many cases environmental (latex) or food (peanuts or shellfish) allergies are just as dangerous (or more so) than drug allergies. These are not always emphasized or are displayed later in the list. There is no way to easily to see that a patient has severe allergies without taking the time to sort through the allergy list.

The display of allergy information for a patient is essential during many aspects of patient care, but for patients with multiple allergies, it is hard to display the entire list of allergies in an application interface all of the time in a way that will be meaningful to a clinician.

Needs exist for improvement in medical software for a mobile device. These, and other needs, are addressed by one or more aspects of the present invention.

SUMMARY OF THE INVENTION

The present invention includes many aspects and features. Moreover, while many aspects and features relate to, and are described in, the context of barcode scanning for medication administration, the present invention is not limited to use only in this context, as will become apparent from the following summaries and detailed descriptions of aspects, features, and one or more embodiments of the present invention.

Accordingly, one aspect of the present invention relates to a method including providing a mobile electronic device disposed within and electronically coupled to a sleeve, wherein the mobile electronic device includes a display disposed on a front side of the mobile electronic device, the sleeve includes a barcode scanner disposed proximate a top side of the sleeve, the mobile electronic device comprises one or more computer readable media containing computer executable instructions for performing a method comprising scanning a barcode using the barcode scanner and accessing medication information associated with the barcode, the sleeve includes light piping; positioning, by a healthcare professional, the electronic device such that the barcode scanner scans a portion of a wristband of a patient which includes a barcode associated with the patient; reading, via the barcode scanner, the barcode associated with the patient; accessing patient information based on the read barcode associated with the patient; positioning, by the healthcare professional, the electronic device such that the barcode scanner scans a portion of a label of a medication container which includes a barcode associated with the medication; reading, via the camera, the barcode associated with the medication; accessing medication information based on the read barcode associated with the medication; automatically determining, based on the accessed patient information and the accessed medication information, whether the medication is the right dose of the right medication for the right patient via the right route at the right time; based on the automatic determination, displaying, to the user, an interface including a text instruction indicating that the medication is okay to administer, and effecting lighting of the light piping as a color coded visual indication corresponding to the text instruction.

In a feature of this aspect, the method further includes providing, by the healthcare professional, the medication to the patient based on the display of the text instruction.

In a feature of this aspect, the mobile electronic device comprises a phone.

In a feature of this aspect, the mobile electronic device comprises a tablet.

In a feature of this aspect, effecting lighting of the light piping as a color coded visual indication corresponding to the text instruction comprises effecting green lighting of the light piping.

In a feature of this aspect, the method includes, based on the automatic determination, effecting an auditory indication corresponding to the text instruction.

In a feature of this aspect, the method includes, following reading, via the barcode scanner, the barcode associated with the patient, effecting lighting of the light piping to indicate a successful reading.

In a feature of this aspect, the method includes, following reading, via the barcode scanner, the barcode associated with the patient, effecting an auditory indication to indicate a successful reading.

Another aspect relates to a method which includes providing a mobile electronic device disposed within and electronically coupled to a sleeve, wherein the mobile electronic device includes a display disposed on a front side of the mobile electronic device, the sleeve includes a barcode scanner disposed proximate a top side of the sleeve, the mobile electronic device comprises one or more computer readable media containing computer executable instructions for performing a method comprising scanning a barcode using the barcode scanner and accessing medication information associated with the barcode, the sleeve includes light piping; positioning, by a healthcare professional, the electronic device such that the barcode scanner scans a portion of a wristband of a patient which includes a barcode associated with the patient; reading, via the barcode scanner, the barcode associated with the patient; accessing patient information based on the read barcode associated with the patient; positioning, by the healthcare professional, the electronic device such that the barcode scanner scans a portion of a label of a medication container which includes a barcode associated with the medication; reading, via the camera, the barcode associated with the medication; accessing medication information based on the read barcode associated with the medication; automatically determining, based on the accessed patient information and the accessed medication information, whether the medication is the right dose of the right medication for the right patient via the right route at the right time; based on the automatic determination, displaying, to the user, an interface including a text instruction indicating that the medication is not the right dose of the right medication for the right patient via the right route at the right time, and effecting lighting of the light piping as a color coded visual indication corresponding to the text instruction.

In a feature of this aspect, effecting lighting of the light piping as a color coded visual indication corresponding to the text instruction comprises effecting yellow lighting of the light piping.

Another aspect relates to a method which includes providing a mobile electronic device disposed within and electronically coupled to a sleeve, wherein the mobile electronic device includes a display disposed on a front side of the mobile electronic device, the sleeve includes a barcode scanner disposed proximate a top side of the sleeve, the mobile electronic device comprises one or more computer readable media containing computer executable instructions for performing a method comprising scanning a barcode using the barcode scanner and accessing medication information associated with the barcode, the sleeve includes light piping; positioning, by a healthcare professional, the electronic device such that the barcode scanner scans a portion of a wristband of a patient which includes a barcode associated with the patient; reading, via the barcode scanner, the barcode associated with the patient; accessing patient information based on the read barcode associated with the patient; positioning, by the healthcare professional, the electronic device such that the barcode scanner scans a portion of a label of a medication container which includes a barcode associated with the medication; reading, via the camera, the barcode associated with the medication; accessing medication information based on the read barcode associated with the medication; automatically determining, based on the accessed patient information and the accessed medication information, whether the medication is the right dose of the right medication for the right patient via the right route at the right time; based on the automatic determination, displaying, to the user, an interface including a text instruction indicating that the medication has not been prescribed for the patient, and effecting lighting of the light piping as a color coded visual indication corresponding to the text instruction.

In a feature of this aspect, effecting lighting of the light piping as a color coded visual indication corresponding to the text instruction comprises effecting red lighting of the light piping.

Another aspect of the present invention relates to a method comprising providing a mobile electronic device including a display disposed on a front side of the electronic device, a camera disposed on a back side of the electronic device, one or more computer readable media containing computer executable instructions for performing a method comprising scanning a barcode using the camera and accessing medication information associated with the barcode; positioning, by a healthcare professional, the electronic device such that the camera captures a first image of a portion of a wristband of a patient which includes a barcode associated with the patient; displaying, on the display of the electronic device, an interface including the captured first image including the portion of the wristband of the patient which includes the barcode associated with the patient; reading, via the camera, the barcode associated with the patient; accessing patient information based on the read barcode associated with the patient; positioning, by the healthcare professional, the electronic device such that the camera captures a second image of a portion of a label of a medication container which includes a barcode associated with the medication; displaying, on the display of the electronic device, an interface including the captured second image including the portion of the label of the medication container which includes the barcode associated with the medication; reading, via the camera, the barcode associated with the medication; accessing medication information based on read barcode associated with the medication; automatically determining, based on the accessed patient information and the accessed medication information, whether the medication is the right dose of the right medication for the right patient via the right route at the right time; displaying, to the user, based on the automatic determinations, an interface including an indication of whether the medication is the right medication, an indication of whether the patient is the right patient, an indication of whether the dose is the right dose, an indication of whether the route is the right route, an indication of whether the time is the right time, a text instruction indicating that the five rights match, that there is a potential overdose, or that medication should not be administered, and a color coded visual indication corresponding to the text instruction.

In a feature of this aspect, the method further includes providing, by the healthcare professional, the medication to the patient based on the display of the text instruction that the five rights match.

In a feature of this aspect, the mobile electronic device comprises a phone.

In a feature of this aspect, the mobile electronic device comprises a tablet.

Another aspect of the present invention relates to a method comprising providing a mobile electronic device including a display disposed on a front side of the electronic device, a camera disposed on a back side of the electronic device, one or more computer readable media containing computer executable instructions for performing a method comprising scanning a barcode using the camera and accessing medication information associated with the barcode; positioning, by a healthcare professional, the electronic device such that the camera captures a first image of a portion of a wristband of a patient which includes a barcode associated with the patient; displaying, on the display of the electronic device, an interface including the captured first image including the portion of the wristband of the patient which includes the barcode associated with the patient; reading, via the camera, the barcode associated with the patient; accessing patient information for the patient based on the read barcode associated with the patient; displaying, to the healthcare professional via the display of the electronic device, a medication administration interface including allergy information for the patient; receiving, from the healthcare professional via one or more input devices associated with the electronic device, first user input corresponding to expansion of a collapsed section of the medication administration interface; expanding, in response to the received first user input, the collapsed section of the medication administration interface such that the section is displayed, the section including vital readings for the patient, and one or more result user interface elements; receiving, from the healthcare professional via one or more input devices associated with the electronic device, second user input corresponding to interaction with one of the one or more result user interface elements; and displaying, in response to the second user input, a modal window including results for the patient.

In a feature of this aspect, the method further includes scanning a medication and providing, by the healthcare professional, the medication to the patient.

In a feature of this aspect, the mobile electronic device comprises a phone.

In a feature of this aspect, the mobile electronic device comprises a tablet.

Accordingly, one aspect of the present invention relates to a method comprising providing an electronic device including a display disposed on a front side of the electronic device, a camera disposed on a back side of the electronic device, one or more computer readable media containing computer executable instructions for performing a method comprising scanning a barcode using the camera and accessing medication information associated with the barcode; positioning, by a healthcare professional, the electronic device such that the camera captures a first image of a portion of a wristband of a patient which includes a barcode associated with the patient; displaying, on the display of the electronic device, an interface, the interface including the captured first image including the portion of the wristband of the patient which includes the barcode associated with the patient, and a text input box configured to allow a user to input a code associated with the patient; reading, via the camera, the barcode associated with the patient; accessing patient information based on the read barcode associated with the patient; positioning, by the healthcare professional, the electronic device such that the camera captures a second image of a portion of a label of a medication container which includes a barcode associated with the medication; displaying, on the display of the electronic device, the interface, the interface including the captured second image including the portion of the label of the medication container which includes the barcode associated with the medication, and a text input box configured to allow a user to input a code associated with the medication; receiving, via a touchscreen of the electronic device, input corresponding to entry of a string into the text input box of the interface, the string representing a code associated with the medication; accessing medication information based on the input string representing a code associated with the medication; displaying, on the display, an indication of the medication and an indication of the patient; providing, by the healthcare professional, the medication to the patient based on the display of the indication of the medication and the indication of the patient.

Another aspect of the present invention relates to a method comprising accessing allergy data for a patient; determining, based on the accessed allergy data, an allergy status for the patient, wherein the allergy status is determined to be severe if a patient has one or more severe allergies, the allergy status is determined to be moderate if the patient has no severe allergies and one or more moderate allergies, the allergy status is determined to be mild if the patient has no severe or moderate allergies and one or more mild allergies; and displaying, to a user via a display associated with an electronic device, an interface of an electronic health record application which includes a patient banner comprising an allergy user interface element indicating the determined allergy status.

Another aspect relates to a method for displaying an indication of the presence and severity of allergies that can be quickly seen without having to review a patient's entire list of allergies.

Another aspect relates to one or more computer readable media containing computer executable instructions for performing a disclosed method.

Another aspect relates to software for facilitating medication administration.

Another aspect relates to one or more computer readable media containing computer executable instructions for facilitating medication administration.

Another aspect relates to a method for facilitating medication administration.

In addition to the aforementioned aspects and features of the present invention, it should be noted that the present invention further encompasses the various possible combinations and subcombinations of such aspects and features. Thus, for example, any aspect may be combined with an aforementioned feature in accordance with the present invention without requiring any other aspect or feature.

BRIEF DESCRIPTION OF THE DRAWINGS

One or more preferred embodiments of the present invention now will be described in detail with reference to the accompanying drawings, wherein the same elements are referred to with the same reference numerals, and wherein.

DETAILED DESCRIPTION

Figure 1:
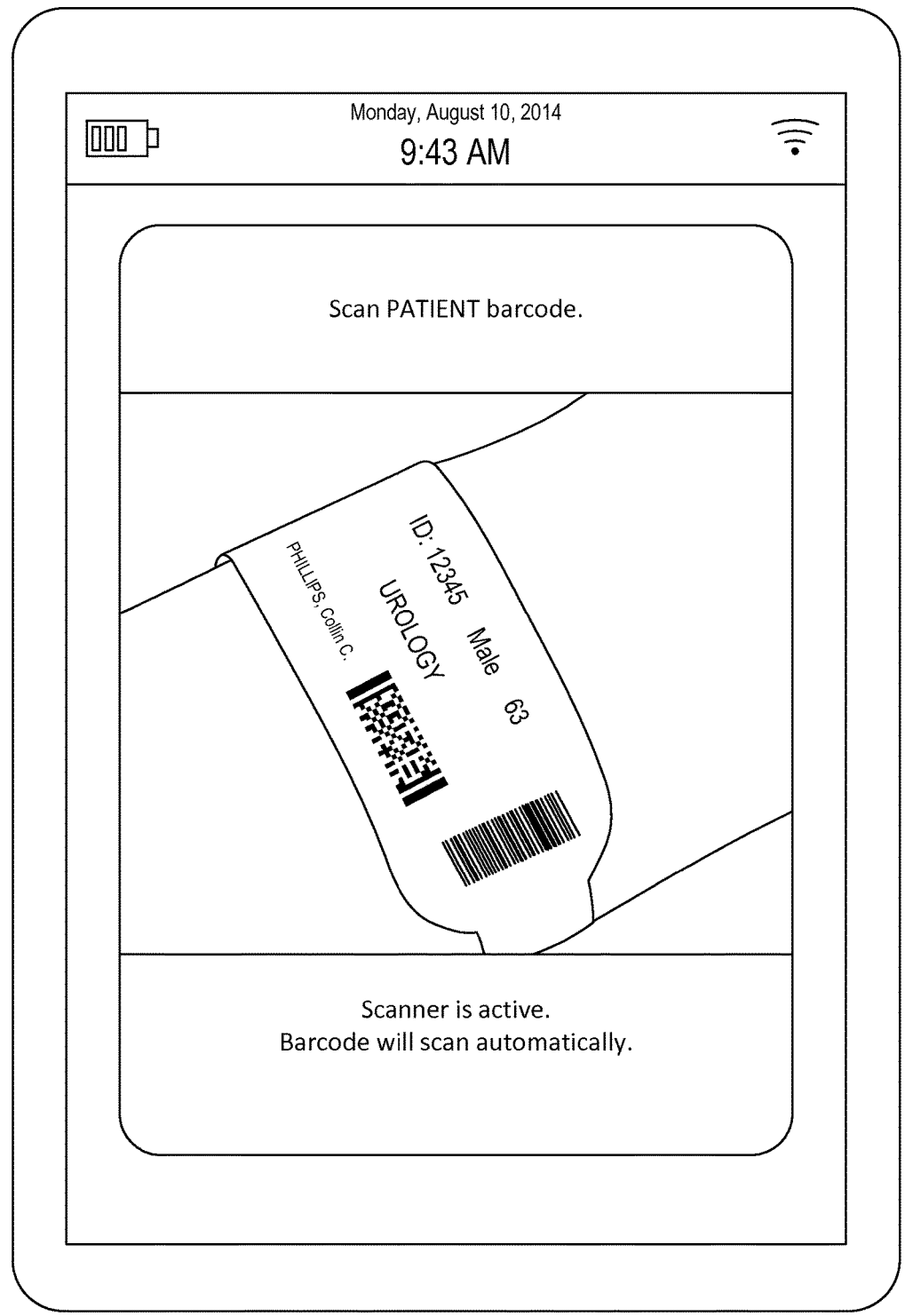
FIG. 1 illustrates an exemplary interface of a software application for a mobile electronic device which is configured to allow a user to scan an electronically readable code on a wristband of a patient.

As a preliminary matter, it will readily be understood by one having ordinary skill in the relevant art ("Ordinary Artisan") that the present invention has broad utility and application. As should be understood, any embodiment may incorporate only one or a plurality of the above-disclosed aspects of the invention and may further incorporate only one or a plurality of the above-disclosed features. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. As should be understood, any embodiment may incorporate only one or a plurality of the above-disclosed aspects of the invention and may further incorporate only one or a plurality of the above-disclosed features. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention in any claim of a patent issuing here from, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the issued claim(s) rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Regarding applicability of 35 U.S.C. § 112, ¶6, no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Referring now to the drawings, one or more preferred embodiments of the present invention are next described. The following description of one or more preferred embodiments is merely exemplary in nature and is in no way intended to limit the invention, its implementations, or uses.

In one or more preferred implementations, medical software is configured to allow a user to scan barcodes to facilitate medication administration. FIG. 1 illustrates an exemplary interface of an electronic device, e.g. a mobile electronic device such as a smart phone or tablet, which is configured to allow a user to scan a barcode, e.g. a barcode on a wristband of a patient or on a medication container or package. In one or more preferred implementations, a mobile electronic device includes a camera disposed on a backside thereof (opposite a display disposed on a front side thereof), and the interface is configured to display video or images captured by the camera so that a user may easily position the mobile electronic device such that the camera can read a barcode on a wristband of a patient. In one or more preferred implementations, a scanning system includes a laser scanner and a computer configured to receive input from the laser scanner.

Figure 2:
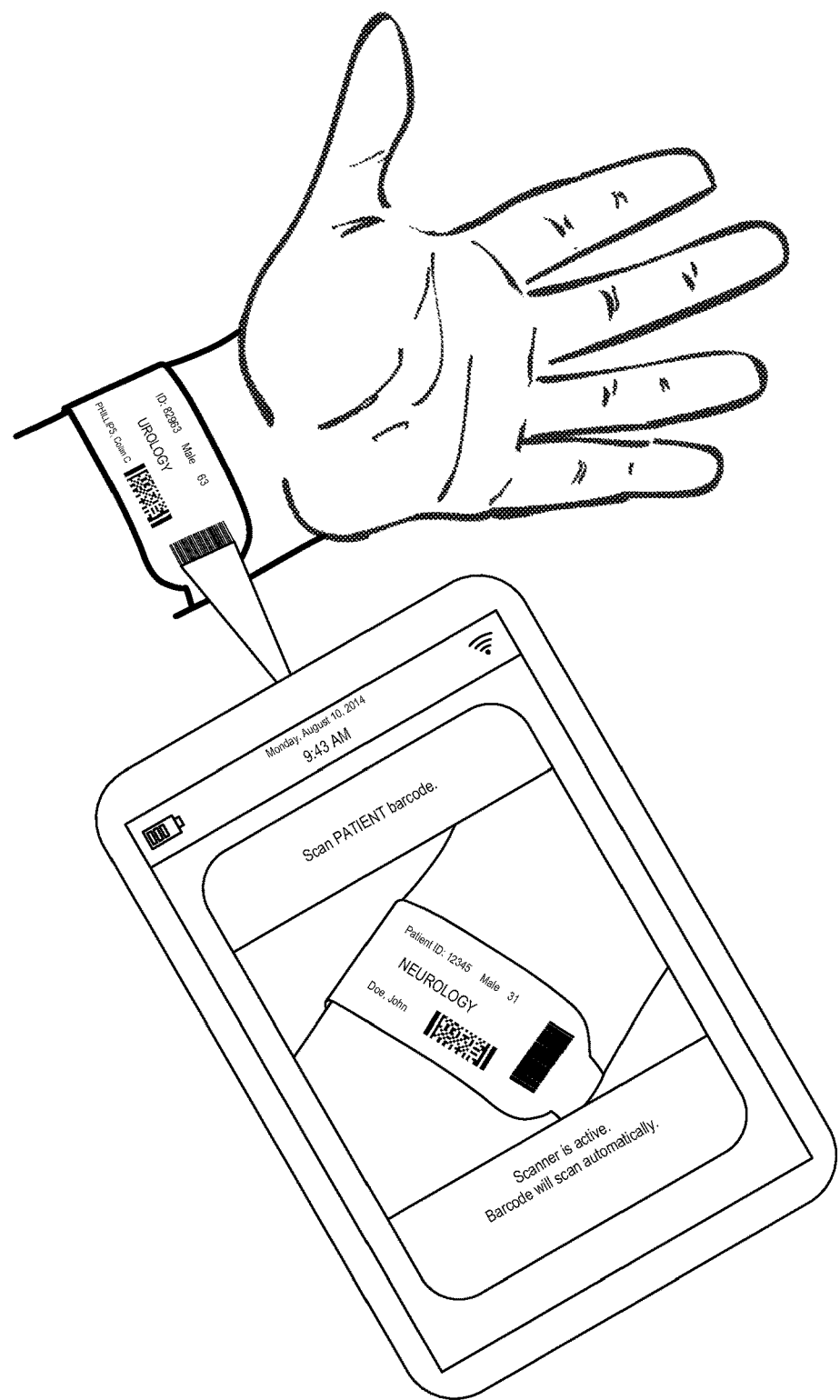
FIG. 2 illustrates use of a scanner disposed proximate a top of a mobile electronic device to scan an electronically readable code on a patient's wrist band.

In one or more preferred implementations, rather than utilizing a camera to scan a barcode, a mobile electronic device utilizes a scanner disposed proximate an edge of the mobile electronic device, as illustrated in FIG. 2. In one or more preferred implementations, a mobile electronic device is disposed within a sleeve such as one available from Infinite Peripherals which includes a laser scanner disposed adjacent a top edge of a mobile electronic device when the mobile electronic device is retained within the sleeve. In one or more preferred implementations, a sleeve is configured for use with an iPad Mini.

In one or more preferred implementations, a sleeve includes light pipes on both sides configured to light up. In one or more preferred implementations, these can light up blue, red, amber, or green. In one or more preferred implementations, a sleeve includes a home button and one or more buttons disposed on a back side thereof. In one or more preferred implementations, one or more buttons disposed on a back side of a sleeve are configured to trigger a scan mode. In one or more preferred implementations, one button on a back side of a sleeve is configured to trigger a scan mode for scanning a barcode associated with a patient, while another button on the back side of the sleeve is configured to trigger a scan mode for scanning a barcode associated with a medication.

In one or more preferred implementations, once a barcode associated with a patient has been scanned, the patient is identified based on that scanned barcode, and patient information associated with that patient is retrieved and preferably displayed. Such identification may occur locally, in a cloud, or at a remote device, such as a server. In one or more preferred implementations, a scanned barcode or input code is utilized to access data stored locally, on a server, in a cloud, in a remote database, in a local database, etc.

Figure 3:
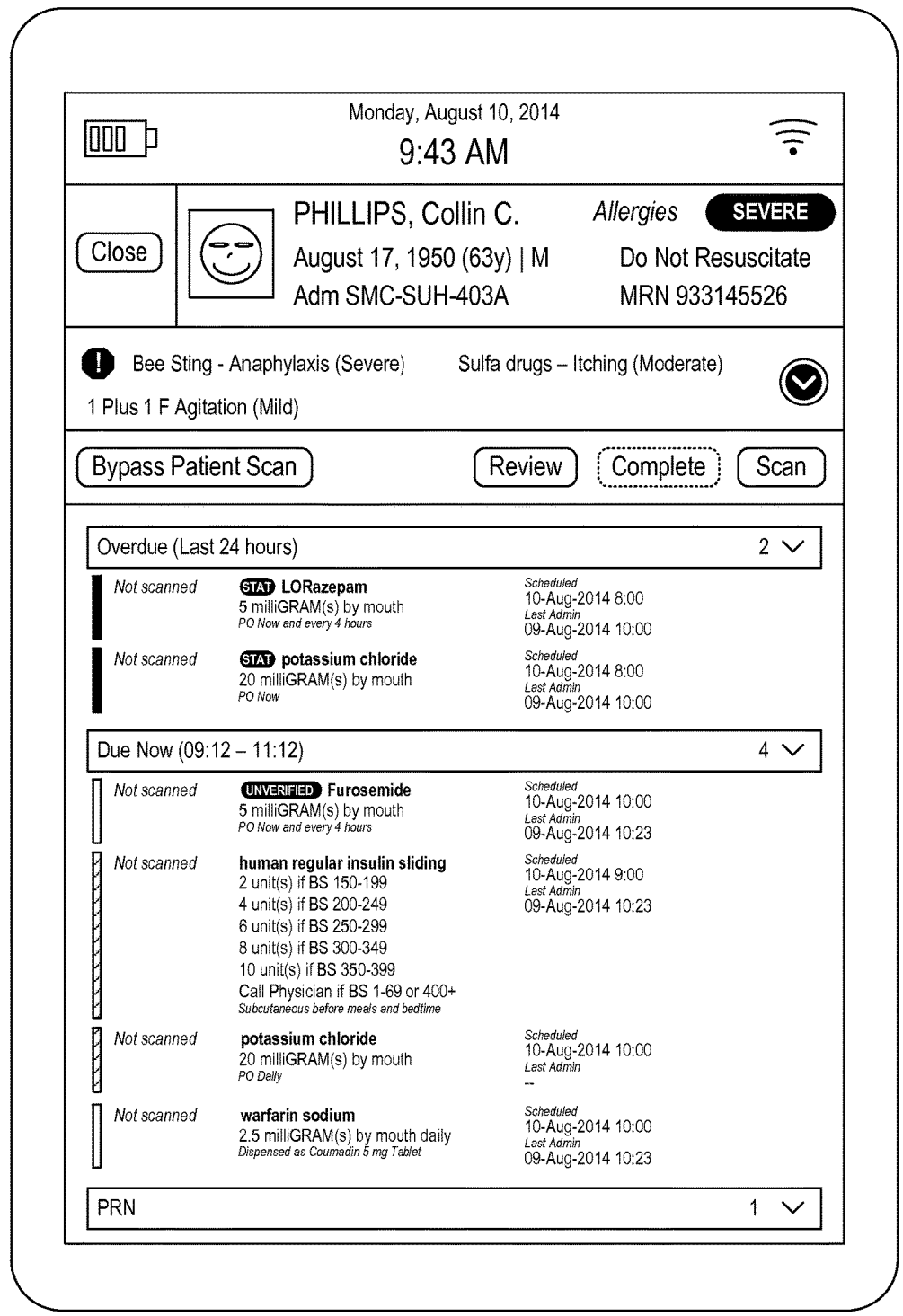
FIGS. 3-8 illustrate exemplary interfaces of a software application for medication administration.

FIG. 3 illustrates a medication administration interface which includes patient information that is displayed in response to scanning of a barcode associated with that patient (although in one or more preferred implementations, this interface may be accessed in another manner, e.g. in response to user input).

The medication administration interface preferably includes allergy information for a patient, including a warning indicator for any severe allergies, as illustrated in FIG. 3.

In one or more preferred implementations, a patient banner includes an allergy graphical user interface element indicating the presence and severity of allergies.

In one or more preferred implementations, the allergy user interface element displays the most severe allergy category for a patient. For example, if a patient has three mild allergies and one severe allergy, the allergy user interface element preferably displays an indication that the patient has a severe allergy.

In one or more preferred implementations, the following different statuses may be displayed by an allergy user interface element.

In one or more preferred implementations, one possible status is a severe status, which preferably is displayed if there are any allergies present with a severity of "severe". FIG. 3 illustrates an exemplary interface including an allergy user interface element indicating that a patient has one or more severe allergies. In one or more preferred implementations, this user interface element is red with white text.

In one or more preferred implementations, another possible status is a moderate status, which preferably is displayed if there are no severe allergies present and one or more allergies present with a severity of "moderate". In one or more preferred implementations, this user interface element is black with orange or yellow text.

In one or more preferred implementations, another possible status is a mild status, which preferably is displayed if there are no severe or moderate allergies present and one or more allergies present with a severity of "mild". In one or more preferred implementations, this user interface element is black with orange or yellow text.

In one or more preferred implementations, another possible status is an unknown status, which indicates the allergy status for a patient has been marked as unknown. In one or more preferred implementations, this user interface element is black with blue text.

In one or more preferred implementations, another possible status is an unassessed status, which indicates the allergy status for a patient has not yet been assessed. In one or more preferred implementations, this user interface element is black with blue text.

In one or more preferred implementations, another possible status is a no known allergies status, which indicates a patient has no known allergies. In one or more preferred implementations, there is not a separate categorization for no known drug allergies, and the presence of a non-drug allergy will take precedence over such a no known drug allergy status. In one or more preferred implementations, this user interface element is black with grey or white text.

The medication administration interface preferably offers one click or touch access to vital readings for a patient, and two click or touch access to orders of a patient. Preferably, all of this information can be accessed without leaving the medication administration interface (and thus interrupting a user's workflow).

Figure 4:
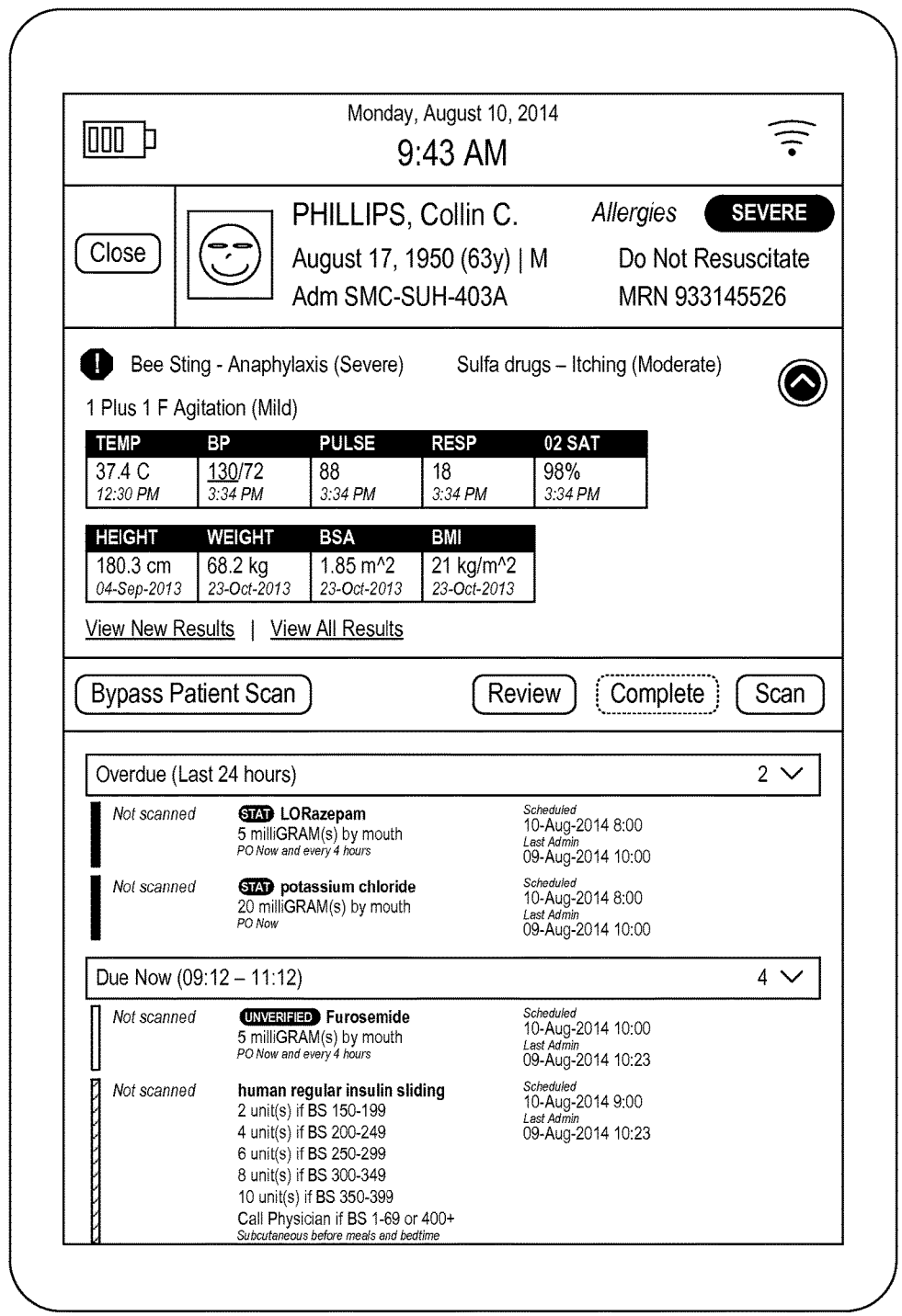

In one or more preferred implementations, vital readings for a patient can be accessed via an expandable section of the medication administration interface. With respect to the exemplary interface of FIG. 3, vital readings can be accessed by clicking or touching the chevron disposed proximate displayed allergy information. FIG. 4 illustrates expansion of a section of the interface to display vital readings. The expanded section of the interface includes results interface elements which allow a user to view results for the patient, e.g. all results or just new results. Preferably, clicking or touching one of these links pops up a modal window including the requested results.

In one or more preferred methodologies of use, a user utilizes the medication administration interface to review allergy information, vital readings, and results without having to navigate away from the medication administration interface.

Figure 5:
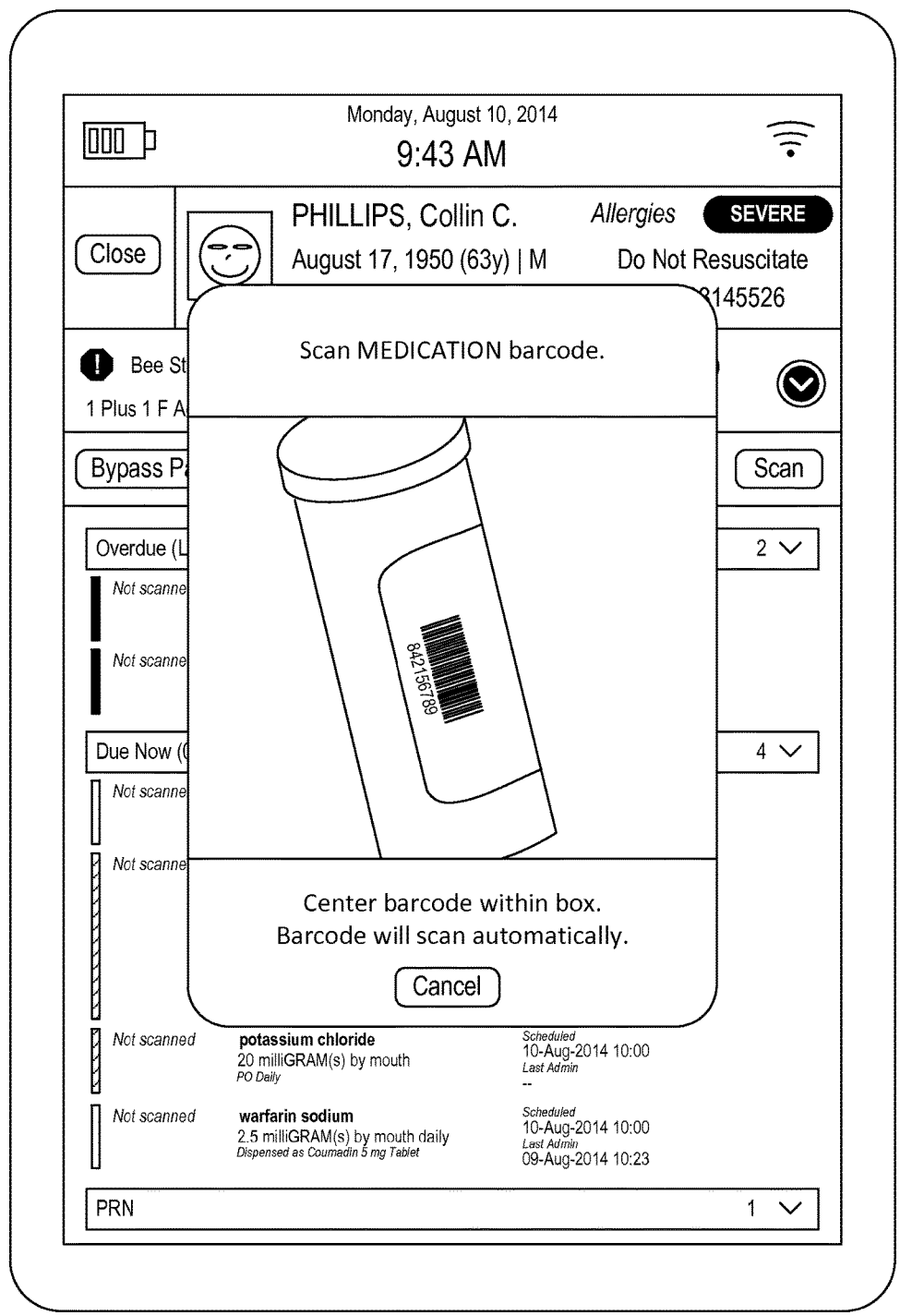

In one or more preferred implementations, from a medication administration interface presenting patient information, a user can utilize a scan interface element to indicate a desire to scan a medication and access a scanning interface configured for scanning a medication barcode, as illustrated in FIG. 5. In one or more preferred implementations, a patient can scan a medication without having to utilize a scan button. In one or more preferred implementation, a user can place the software into a scan mode by pressing a button disposed on a back side of a sleeve a mobile device is disposed in.

In one or more preferred implementations, once a barcode associated with a medication has been scanned, the medication is identified based on that scanned barcode, and the system uses retrieved medication information and patient information to attempt to automatically confirm the "five rights" of medication administration. Such identification, retrieval, and confirmation may occur locally or at a remote device, such as a server.

Figure 6:
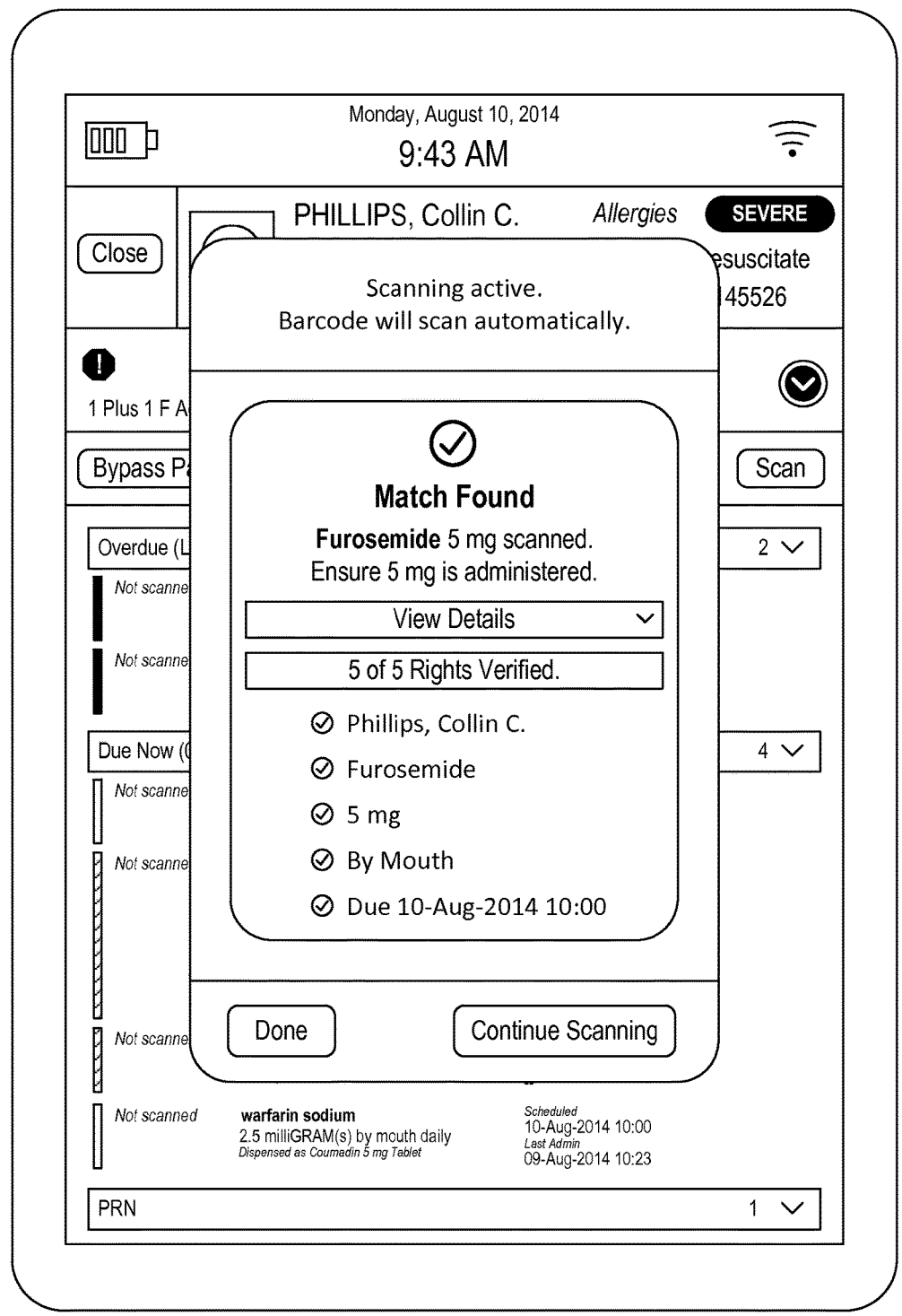
Figure 7:
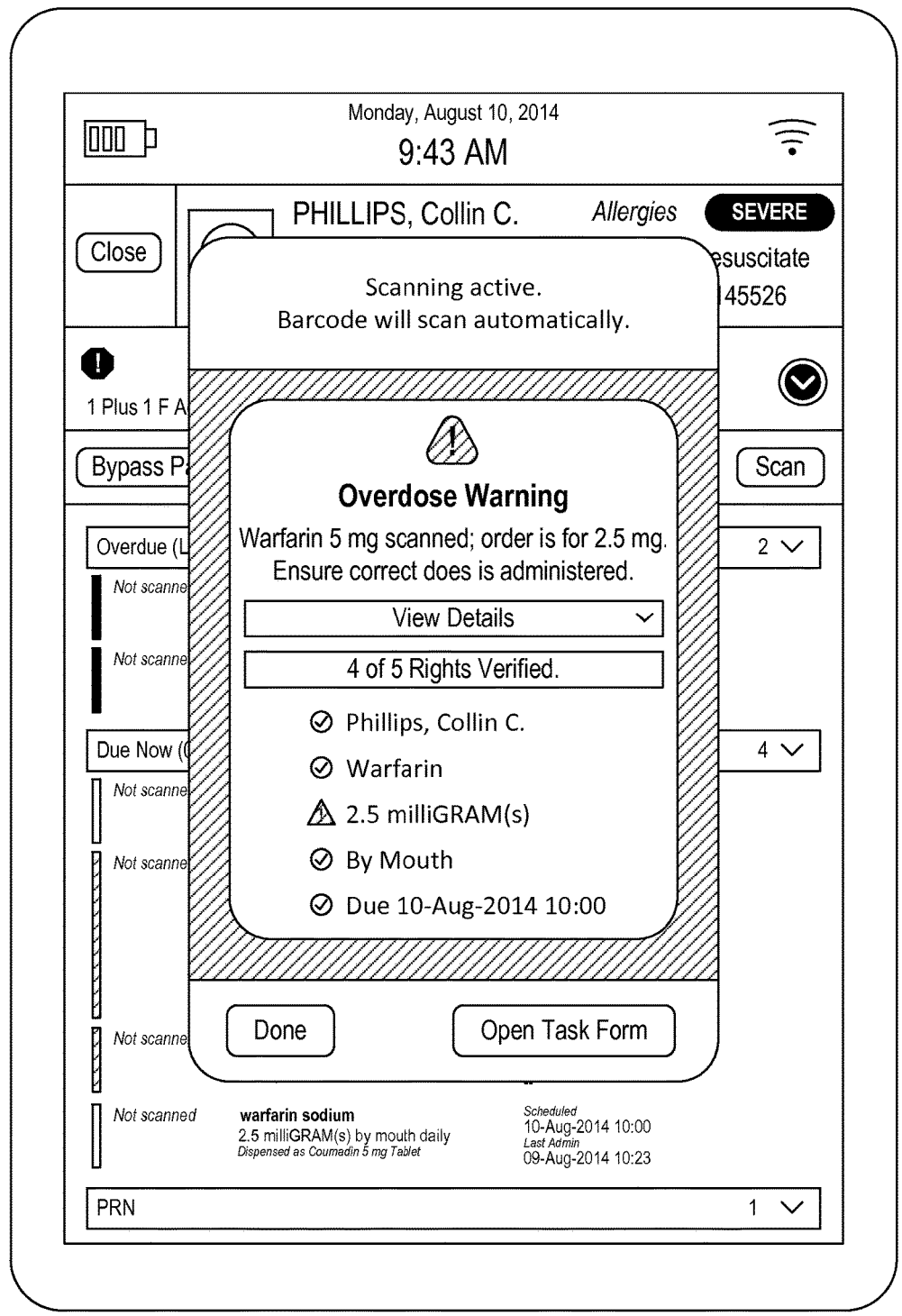
Figure 8:
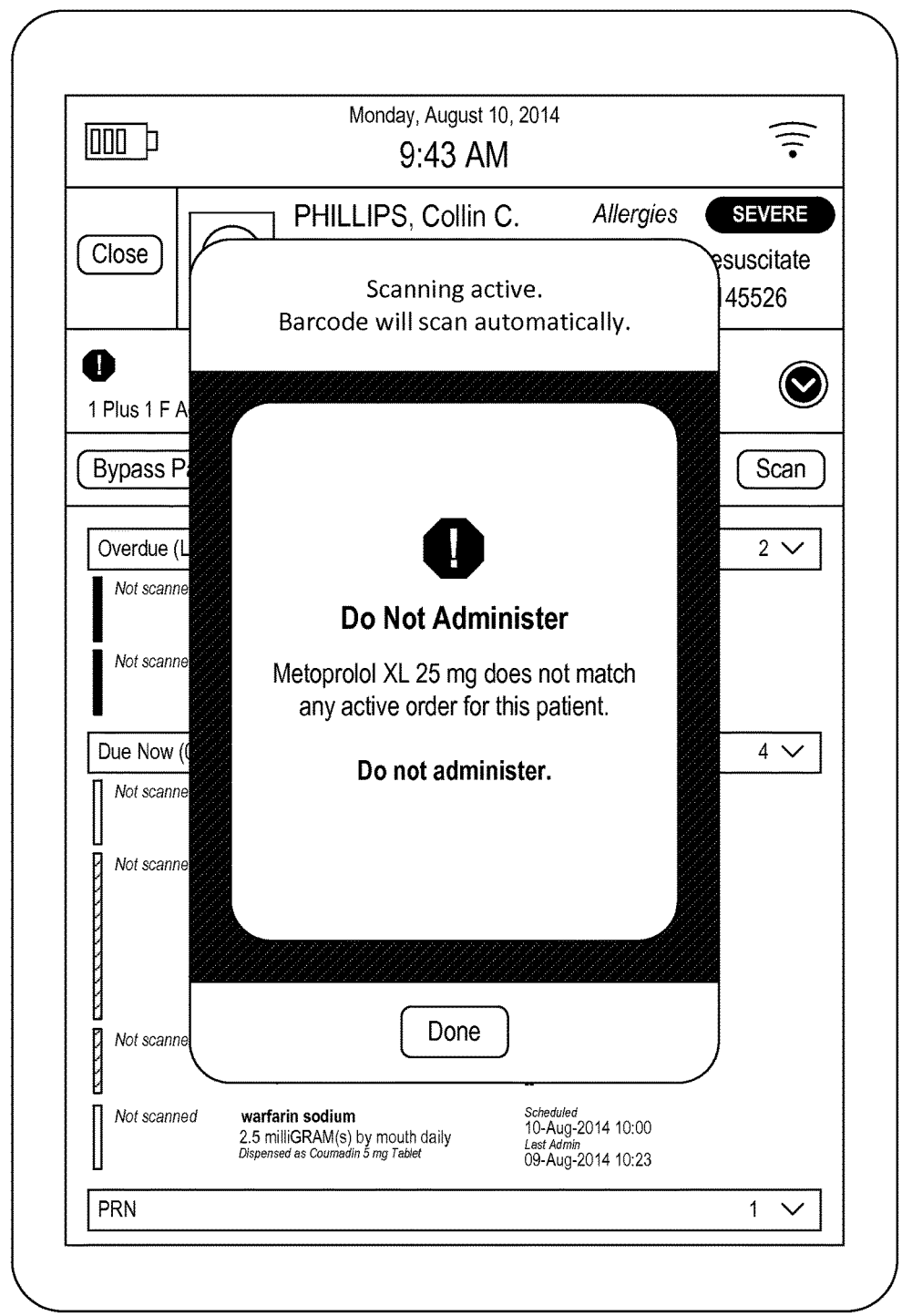

Preferably, the information corresponding to results of the automatic attempt to confirm the "five rights" is displayed to a user via an interface, as illustrated in FIGS. 6-8.

In one or more preferred implementations, a system will check a medication list associated with a patient to determine that the medication scanned was ordered for the scanned patient. Preferably, an interface confirming scans will display the "five rights" verification to the user so that it is clear whether or not it is safe to give the medication as scanned. Preferably, each of the rights displays separately and will show whether or not the match is correct. Preferably, a green check will display for matches and a warning icon will display next to any discrepancies in the "five rights".

In one or more preferred implementations, if all of the rights are correct, the scan dialog will display with a green border, while if any of the rights are not correct, the scan dialog will display with a yellow border, drawing your attention to the fact there is something that needs to be addressed. Preferably, if the medication is not ordered for the patient, then the dialog will display with a red border and a message will instruct the user to not give the medication. In one or more preferred implementations in which a mobile device is disposed within a sleeve including light piping, lights disposed on the sleeve will light up the corresponding color. In one or more preferred implementations, an auditory indicator will be provided as well. In one or more preferred implementations, each possible status has its own corresponding auditory indicator, while in one or more preferred implementations "green" and "yellow" statuses may share a single auditory indicator. In one or more preferred implementations, a successful scan will be indicated by an auditory indicator that is distinct from an auditory indicator associated with a "green", "yellow", or "red" status.

Notably, in one or more preferred implementations, from a medication administration interface presenting patient information, a user can utilize a scan interface element to indicate a desire to scan another patient and access a scanning interface configured for scanning a patient barcode. In one or more preferred implementations, the same interface might be configured for scanning of both patient and medication barcodes, as illustrated in FIG. 9.

Figure 9:
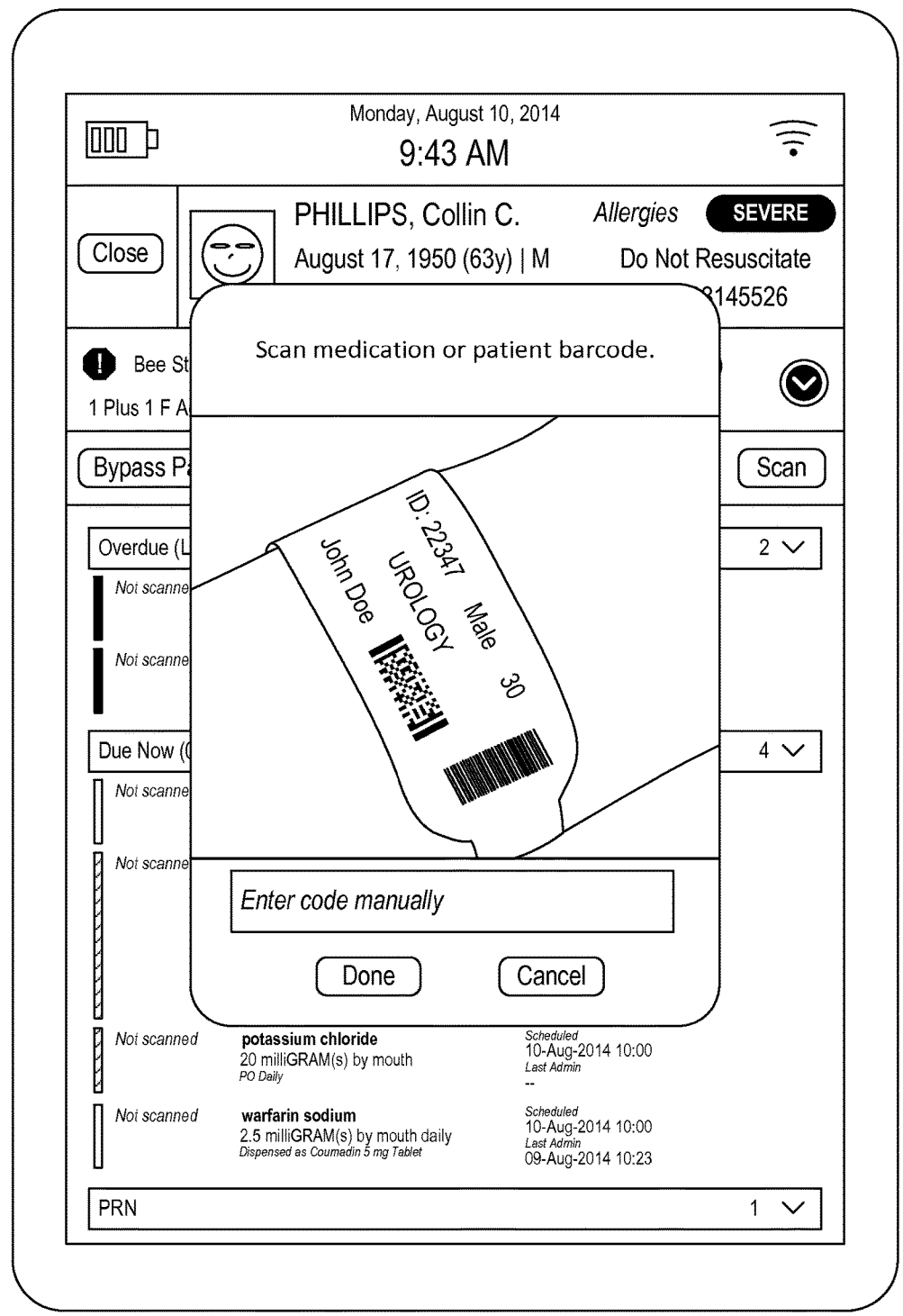
FIG. 9 illustrates an exemplary interface of a software application configured for scanning of an electronically readable code which is configured to allow for manual input of a code.

In one or more preferred implementations, an interface which is configured to allow for automatic barcode scanning is further configured to allow a user to bypass automatic scanning by manually entering a code without having to leave the interface configured to allow for automatic scanning FIG. 9 illustrates an exemplary such interface which includes a text box which allows a user to manually input a code. If a user wants to bypass automatic scanning (e.g. because it is not working), the user can manually input a code into the text box and then effect pressing of the associated "Done" button.

In an exemplary methodology in accordance with one or more preferred implementations, a user inserts a mobile electronic device into a sleeve which includes a scanner and light piping. The sleeve preferably lights up blue to indicate a successful connection. Thereafter, the user utilizes the scanner to scan a barcode or other electronically readable code printed on a patient's wristband. A successful scan causes the light piping on the sleeve to flash green, and patient information is displayed on the mobile electronic device. An auditory tone may also indicate such successful scan. Next, the user scans a barcode or other electronically readable code associated with a medication. Preferably, an auditory tone confirms the successful scan, and software attempts to confirm that the medication is the right medication for the right patient at the right time at the right dose via the right route. A visual indication is preferably displayed as to whether all five of the "rights" checked out, light piping on the sleeve lights up to quickly indicate whether medication should be administered, and a corresponding auditory tone is emitted.

In one or more preferred implementations, auditory tones associated with described software override any current sound settings on a device, such as, for example, a mute setting or a low volume setting.

In one or more preferred implementations, a software application is configured for installation on an off-the-shelf commercial mobile electronic device, e.g. via download from an app store.

In one or more preferred implementations, setting a mobile electronic device face down locks a software application configured to provide a medication administration interface as disclosed herein.

In one or more preferred implementations, a scanned barcode or input code is utilized to access data stored locally, on a server, in a cloud, in a remote database, in a local database, etc.

Based on the foregoing description, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention. Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements, the present invention being limited only by the claims appended hereto and the equivalents thereof.

What is claimed is:

1. A method comprising:
(a) providing a mobile electronic device disposed within and electronically coupled to a sleeve, wherein
  (i) the mobile electronic device includes a display disposed on a front side of the mobile electronic device,
  (ii) the sleeve includes a barcode scanner disposed proximate a top side of the sleeve,
  (iii) the sleeve includes first and second buttons disposed on a back side of the sleeve,
  (iv) the mobile electronic device comprises one or more computer readable media containing computer executable instructions for scanning barcodes using the barcode scanner and accessing information based thereon,
  (iv) the sleeve includes light piping;
(b) receiving, at the mobile electronic device, an indication of user input in the form of pressing of the first button disposed on the back side of the sleeve, and based thereon, triggering a first scan mode for scanning a patient barcode;
(c) positioning, by a healthcare professional, the electronic device such that the barcode scanner scans a portion of a wristband of a patient which includes a barcode associated with the patient;
(d) reading, via the barcode scanner, the barcode associated with the patient;
(e) accessing patient information based on the read barcode associated with the patient;
(f) receiving, at the mobile electronic device, an indication of user input in the form of pressing of the second button disposed on the back side of the sleeve, and based thereon, triggering a second scan mode for scanning a medication barcode;
(g) positioning, by the healthcare professional, the electronic device such that the barcode scanner scans a portion of a label of a medication container which includes a barcode associated with the medication;
(h) reading, via the barcode scanner, the barcode associated with the medication;
(i) accessing medication information based on the read barcode associated with the medication;
(j) automatically determining, based on the accessed patient information and the accessed medication information, whether the medication is the right dose of the right medication for the right patient via the right route at the right time;
(k) based on the automatic determination,
  (ii) displaying, to the user, an interface including a text instruction indicating that the medication is okay to administer, and
  (ii) effecting lighting of the light piping as a color coded visual indication corresponding to the text instruction.

2. The method of claim 1, wherein the method further includes providing, by the healthcare professional, the medication to the patient based on the display of the text instruction.

3. The method of claim 1, wherein the mobile electronic device comprises a phone.

4. The method of claim 1, wherein the mobile electronic device comprises a tablet.

5. The method of claim 1, wherein effecting lighting of the light piping as a color coded visual indication corresponding to the text instruction comprises effecting green lighting of the light piping.

6. The method of claim 1, wherein the method includes, based on the automatic determination, effecting an auditory indication corresponding to the text instruction.

7. The method of claim 1, wherein the method includes, following reading, via the barcode scanner, the barcode associated with the patient, effecting lighting of the light piping to indicate a successful reading.

8. The method of claim 1, wherein the method includes, following reading, via the barcode scanner, the barcode associated with the patient, effecting an auditory indication to indicate a successful reading.

9. A method comprising:
(a) providing a mobile electronic device disposed within and electronically coupled to a sleeve, wherein
  (i) the mobile electronic device includes a display disposed on a front side of the mobile electronic device,
  (ii) the sleeve includes a barcode scanner disposed proximate a top side of the sleeve,
  (iii) the sleeve includes first and second buttons disposed on a back side of the sleeve,
  (iv) the mobile electronic device comprises one or more computer readable media containing computer executable instructions for scanning barcodes using the barcode scanner and accessing information based thereon,
  (iv) the sleeve includes light piping;
(b) receiving, at the mobile electronic device, an indication of user input in the form of pressing of the first button disposed on the back side of the sleeve, and based thereon, triggering a first scan mode for scanning a patient barcode;
(c) positioning, by a healthcare professional, the electronic device such that the barcode scanner scans a portion of a wristband of a patient which includes a barcode associated with the patient;
(d) reading, via the barcode scanner, the barcode associated with the patient;
(e) accessing patient information based on the read barcode associated with the patient;
(f) receiving, at the mobile electronic device, an indication of user input in the form of pressing of the second button disposed on the back side of the sleeve, and based thereon, triggering a second scan mode for scanning a medication barcode;
(g) positioning, by the healthcare professional, the electronic device such that the barcode scanner scans a portion of a label of a medication container which includes a barcode associated with the medication;
(h) reading, via the barcode scanner, the barcode associated with the medication;

(i) accessing medication information based on the read barcode associated with the medication;
(j) automatically determining, based on the accessed patient information and the accessed medication information, whether the medication is the right dose of the right medication for the right patient via the right route at the right time;
(k) based on the automatic determination,
  (i) displaying, to the user, an interface including a text instruction indicating that the medication is not the right dose of the right medication for the right patient via the right route at the right time, and
  (ii) effecting lighting of the light piping as a color coded visual indication corresponding to the text instruction.

10. The method of claim 9, wherein the mobile electronic device comprises a phone.

11. The method of claim 9, wherein the mobile electronic device comprises a tablet.

12. The method of claim 9, wherein effecting lighting of the light piping as a color coded visual indication corresponding to the text instruction comprises effecting yellow lighting of the light piping.

13. The method of claim 9, wherein the method includes, based on the automatic determination, effecting an auditory indication corresponding to the text instruction.

14. The method of claim 9, wherein the method includes, following reading, via the barcode scanner, the barcode associated with the patient, effecting lighting of the light piping to indicate a successful reading.

15. The method of claim 9, wherein the method includes, following reading, via the barcode scanner, the barcode associated with the patient, effecting an auditory indication to indicate a successful reading.

16. A method comprising:
(a) providing a mobile electronic device disposed within and electronically coupled to a sleeve, wherein
  (i) the mobile electronic device includes a display disposed on a front side of the mobile electronic device,
  (ii) the sleeve includes a barcode scanner disposed proximate a top side of the sleeve,
  (iii) the sleeve includes first and second buttons disposed on a back side of the sleeve,
  (iv) the mobile electronic device comprises one or more computer readable media containing computer executable instructions for scanning barcodes using the barcode scanner and accessing information based thereon,
  (iv) the sleeve includes light piping;
(b) receiving, at the mobile electronic device, an indication of user input in the form of pressing of the first button disposed on the back side of the sleeve, and based thereon, triggering a first scan mode for scanning a patient barcode;
(c) positioning, by a healthcare professional, the electronic device such that the barcode scanner scans a portion of a wristband of a patient which includes a barcode associated with the patient;
(d) reading, via the barcode scanner, the barcode associated with the patient;
(e) accessing patient information based on the read barcode associated with the patient;
(f) receiving, at the mobile electronic device, an indication of user input in the form of pressing of the second button disposed on the back side of the sleeve, and based thereon, triggering a second scan mode for scanning a medication barcode; (g) positioning, by the healthcare professional, the electronic device such that the barcode scanner scans a portion of a label of a medication container which includes a barcode associated with the medication;
(h) reading, via the barcode scanner, the barcode associated with the medication;
(i) accessing medication information based on the read barcode associated with the medication;
(j) automatically determining, based on the accessed patient information and the accessed medication information, whether the medication is the right dose of the right medication for the right patient via the right route at the right time;
(k) based on the automatic determination,
  (i) displaying, to the user, an interface including a text instruction indicating that the medication has not been prescribed for the patient, and
  (ii) effecting lighting of the light piping as a color coded visual indication corresponding to the text instruction.

17. The method of claim 16, wherein the mobile electronic device comprises a phone.

18. The method of claim 16, wherein the mobile electronic device comprises a tablet.

19. The method of claim 16, wherein effecting lighting of the light piping as a color coded visual indication corresponding to the text instruction comprises effecting red lighting of the light piping.

20. The method of claim 16, wherein the method includes, based on the automatic determination, effecting an auditory indication corresponding to the text instruction.

* * * * *